United States Patent
Grant et al.

(10) Patent No.: US 6,926,905 B2
(45) Date of Patent: Aug. 9, 2005

(54) LIPOSOMAK COMPOSITIONS AND METHODS OF PREPARATION

(75) Inventors: Gilbert J. Grant, White Plains, NY (US); Elijah M. Bolotin, Buffalo Grove, IL (US); Yechezkel Barenholz, Jerusalem (IL); Herman Turndorf, New York, NY (US)

(73) Assignees: Yissum Research Development Company of the Hebrew University of Jerusalem, Jerusalem (IL); New York University, New York, NY (US)

( * ) Notice: Subject to any disclaimer, the term of this patent is extended or adjusted under 35 U.S.C. 154(b) by 0 days.

(21) Appl. No.: 10/620,006

(22) Filed: Jul. 16, 2003

(65) Prior Publication Data

US 2004/0018230 A1 Jan. 29, 2004

Related U.S. Application Data

(63) Continuation of application No. 09/646,994, filed as application No. PCT/US99/06959 on Mar. 30, 1999, now abandoned.
(60) Provisional application No. 60/080,195, filed on Mar. 31, 1998.

(51) Int. Cl.[7] .............................................. A61K 9/127
(52) U.S. Cl. .................... 424/450; 264/4.1; 264/4.3; 264/4.6; 424/417
(58) Field of Search ................................ 424/450, 417, 424/1.21, 9.321, 9.51; 264/4.1, 4.3, 4.6

(56) References Cited

U.S. PATENT DOCUMENTS

| 4,844,904 A | 7/1989 | Hamaguchi |
| 5,244,678 A | 9/1993 | Legros et al. |
| 5,626,832 A | 5/1997 | Schneider |

FOREIGN PATENT DOCUMENTS

| EP | 0561424 A1 | 9/1993 |
| WO | WO 9742936 A1 | 11/1997 |

OTHER PUBLICATIONS

Stewart, James C.M., Colorimetric Determination of Phospholipids with Ammonium Ferrothicyanate, Analytical Biochemistry, May 1, 1980, pp. 10–14. PMID: 6892980 [PubMed—Indexed for MEDLINE].
Bartlett, Grant R., Phosphorus assay in Column Chromatography, Aug. 4, 1958, J. Biol. Chem., 234, pp. 466–468.
Kirby in Biotechnology, Nov. 1984, pp. 979–984.

*Primary Examiner*—Gollamudi S. Kishore
(74) *Attorney, Agent, or Firm*—Browdy and Neimark, P.L.L.C.

(57) ABSTRACT

Long-term local anesthesia is provided by administering to a subject in need thereof a liposomal anesthetic formulation prepared by the dehydration-rehydration method. In this method, lyophilized liposomes encapsulating the local anesthetic are rehydrated by agitating them in an aqueous medium. Preferably this method includes the further step of washing the rehydrated liposomes in hyperosmotic saline solution.

12 Claims, 2 Drawing Sheets

LIPOSOMAK COMPOSITIONS AND METHODS OF PREPARATION

CROSS-REFERENCE TO RELATED APPLICATION

The present application is a continuation of U.S. Ser. No. 09/646,994, filed Nov. 20, 2000, abandoned which is the National Stage of PCT/US99/06959 filed Mar. 30, 1999, which claims the benefit of 60/080,195 filed on Mar. 31, 1998, the entire contents of which are hereby incorporated.

FIELD OF THE INVENTION

The present invention is directed to liposomal compositions of local anesthetics, such as bupivacaine, and in particular to DRV (dehydration-rehydration vesicle) compositions and methods of their preparation and use.

BACKGROUND OF THE INVENTION

Long acting local anesthetic formulations hold great promise for the management of acute pain, as long lasting analgesia could be achieved with a single dose administered after surgery or trauma. Liposomal local anesthetic formulations have been shown to prolong analgesic duration in animals (Grant et al.; Mowat et al., Boogaerts, Declercq et al., 1993) and humans (Boogaerts, Lafont et al., 1996). The slow release of drug from the liposomal depot decreases the potential for systemic toxicity, and allows for administration of a greater dose. The effectiveness of liposomal bunivacaine in providing prolonged analgesia in a rat postoperative wound model has been demonstrated (Grant el al.). Formulations described to date, however, have drug-to-lipid ratios, which are too low to be clinically useful in humans.

Further issues must also be resolved before liposomal local anesthetics can be used to manage acute pain in patients. Critical requirements for a liposomal formulation include reliability and reproducibility in manufacturing and performance, and adequate shelf stability to permit long term storage. Liposomal local anesthetic compositions, which have been described in the literature, employ multi-lamellar vesicles (MLV) and large unilamellar vesicles (LUV). These liposomes are stored in aqueous media, whereby the component lipids are subject to degradation due to oxidation and hydrolysis. Moreover, encapsulated drug may leak from the liposome into the aqueous medium.

It is therefore desirable to provide a liposomal anesthetic formulation which has a high loading of drug, relative to total lipids and to total volume, and which has long term storage stability.

SUMMARY OF THE INVENTION

In one aspect, the invention provides a method of providing long term local anesthesia, comprising administering to a subject in need of such treatment a liposomal local anesthetic formulation prepared by the dehydration-rehydration method, in which lyophilized liposomes encapsulating the local anesthetic are rehydrated by agitating in an aqueous medium. Preferably, the preparation includes the further step of washing the rehydrated liposomes in hyperosmotic saline solution. An exemplary local anesthetic is bupivacaine. Other local anesthetics which may be used, as discussed further below, include lidocaine, ropivacaine, levobupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine.

More generally, the invention provides a method of preparing a liposomal drug composition having a high drug/lipid ratio, comprising the steps of encapsulating the drug in liposomes, lyophilizing the liposomes, rehydrating the lyophilized liposomes by agitating in an aqueous medium, and washing the rehydrated liposomes in hyperosmotic saline solution. In one embodiment, the drug is a local anesthetic, such as bupivacaine.

In a related aspect, the invention provides a liposomal local anesthetic composition having a high drug/lipid ratio, where the local anesthetic is preferably bupivacaine, and the drug/lipid ratio is preferably at least 0.3 (mole/mole), and more preferably at least 0.33 (mole/mole). Such liposomal local anesthetic compositions are prepared by encapsulating the local anesthetic in liposornes, lyophilizing the liposornes, and rehydrating the lyophilized liposomes by agitating in an aqueous medium, and washing the rehydrated liposomes in hyperosmotic saline solution.

DETAILED DESCRIPTION OF THE INVENTION

I. DRV (Dehydration-Rehydration) Liposomes

A. Preparation

Figure 1:
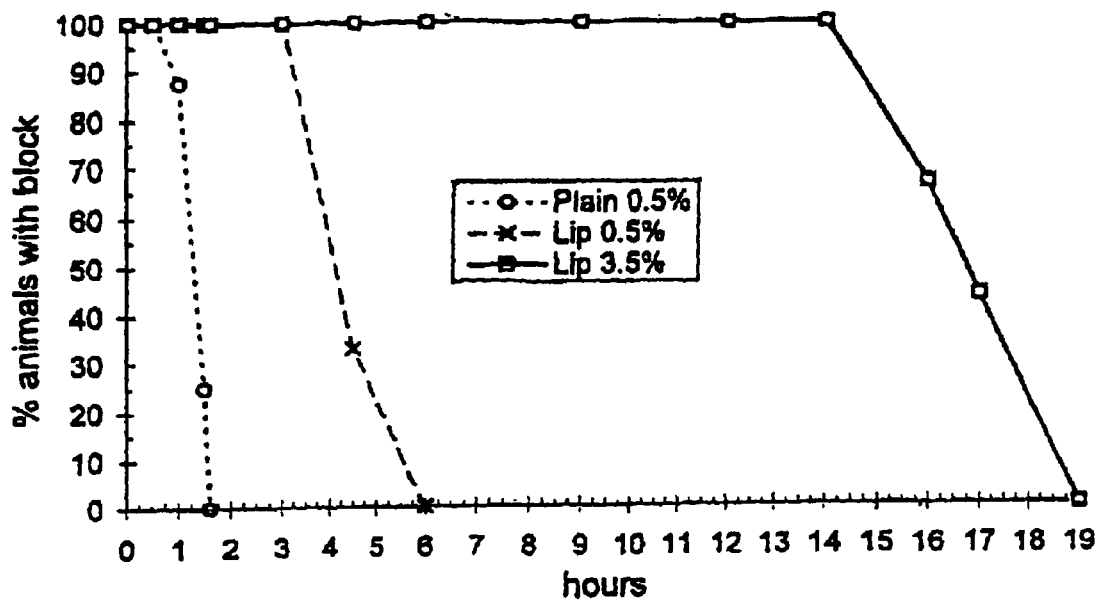
FIG. 1 shows the duration of sensory block observed in mice after administration of 0.5% free, 0.5% liposomal (DRV), and 3.5% liposomal bupivacaine (BUP).

Bupivacaine hydrochloride (BUP) (Sigma, St. Louis, Mo.) was encapsulated into liposomes by the dehydration-rehydration (DRV) technique, as described, for example, in Kirby et al. Dehydrated-rehydrated vesicles (DRVs) are liposomes which can be reproducibly prepared, stored in a lyophilized state, and rehydrated immediately prior to administration (Kirby). Maintaining the formulations in the dehydrated state greatly reduces the likelihood of degradation, and confers shelf stability (Zuidam).

Two different matrix lipids were used: 1,2-dimyristoyl-sn-glycero-3-phosphatidylcholine (DMPQ and distearoyl-sn-glycero-3-phosphatidylcholine (DSPQ (Avanti Polar Lipids, Alabaster, Ala.). DMPC, having a gel-to-liquid-crystalline phase transition temperature (Tm) of 23° C., tends to give a more fluid membrane, while DSPC, having a Tm of 52.5° C., gives a more rigid membrane, as discussed further below.

Twenty or forty mole % cholesterol (CHOL, Sigma, St. Louis, Mo.) was used in combination with each phospholipid. Two different molar ratios of BUP/lipid (0.64 and 1.28) were employed, as well as two different pH levels.

For DRV preparation, DMPC or DSPC and CHOL were co-dissolved in tert-butanol (Fisher, Pittsburgh, Pa.) and lyophilized. The dried lipid was hydrated with water at 60° C. to form multilamellar vesicles (MLV). Small unilamellar vesicles (SUVs) were prepared by highpressure (8,000–10,000 psi) homogenization (Minilab 8.30H, APV Rannie, Albertslund, Denmark). SUV size was confirmed to be approximately 100 nm by photon correlation spectroscopy (N4 Plus, Coulter, Miami, Fla.). BUP was dissolved in the SUVs at pH 4.0 or 5.5. The solution was then divided, transferred to glass bottles, frozen and lyophilized overnight.

To prepare DRV formulations, the lyophilized powder was hydrated with saline while vortexing at 60° C. to achieve a final lipid concentration of 10%. Prior to characterization and injection, free drug was removed from the final liposomal formulations by 4 successive centrifugal washings with normal saline at 4° C., followed by a final wash with hyperosmotic saline (580 mM) at 4° C. As noted below, use of this final wash of hyperosmotic saline, e.g. having a concentration of about 300 to 600 mM NaCl, was found to give a very high final concentration of drug in the liposomal formulation.

B. Characterization: Bupivacaine Incorporation

BUP concentration in the liposomes was determined by high performance liquid chromatography (HPLC). Isopropanol (1:1000) was used to dissolve washed liposomes, and aliquots were injected onto an 8-mm×100-mm column (Radial-Pak 8NVCN, 4 mm, Waters, Milford, Mass.). A mobile phase of acetonitrile: phosphate buffer, 25 mM, pH 4.0 (75:25) was used, and absorption was measured at a wavelength of 210 nm. The retention time of BUP was approximately 4.7 min. Phospholipid concentration was determined using procedures described in Bartlett or Stewart. The BUP to phospholipid ratio (BUP/PQ was then calculated.

The size of the multilamellar DRV liposomes was determined by photon correlation spectroscopy spectroscopy (N4 Plus, Coulter, Miami, Fla.). The size distributions of all formulations were similar; the mean diameter of liposomes of formulation 3 was 1931±722 nm.

All in vitro liposomal characterization procedures were performed in triplicate. Results are summarized in Table 1.

TABLE 1

| Formulation | Matrix Lipid | Mole % Chol | Added Bup, mg (molar ration) | Final Bup concn, mg/ml | Drug to PC ratio, mM/mM |
|---|---|---|---|---|---|
| 1 | DSPC | 40 | 40 (1.28) | 17 | .116 |
| 2 | DSPC | 40 | 20 (0.64) | 19 | .127 |
| 3 | DSPC | 20 | 40 | 35 | .356 |
| 4 | DSPC | 20 | 20 | 29 | .257 |
| 5 | DMPC | 40 | 40 | 4 | .024 |
| 6 | DMPC | 40 | 20 | 5 | .023 |

As shown in the Table, liposomes prepared with DSPC as the matrix lipid (formulations 1–4) had higher BUP/PL ratios. The two BUP concentrations resulted in similar BUP/PL ratios. In preliminary studies, the pH of the solution did not affect final BUP/PL ratio, so all subsequent work was done at pH 5.5.

The choice of matrix lipid markedly affected BUP/PL ratio, with DSPC resulting in more effective BUP encapsulation than DMPC. As noted above, the higher Tm of DSPC tends to give a more rigid liposome at ambient temperature, which may prevent loss of BUP during washings.

For DSPC liposomes, lower % cholesterol (formulations 2–3) resulted in greater BUP/PL ratios. Accordingly, still lower levels of cholesterol may be used. For DMPC, on the other hand, lower % cholesterol resulted in very low BUP/PL ratios (data not shown). Cholesterol is known to increase membrane rigidity, and therefore may have reduced leakage of the less rigid DMPC liposomes. In the case of the more rigid DSPC liposomes, it is possible that BUP and CHOL compete for the same sites in the bilayer.

Formulation 3 gave a drug/PC ratio of about 0.36, which is much higher than previously reported for MLV loaded by standard methods (e.g. about 0.1, reported by F. Legros et al.), and even higher than reported for remote loading using sodium citrate, (about 0.26). A high drug-to-lipid ratio is especially important in treatment of superficial wounds, where a high amount of lipid residue is undesirable.

Using hyperosmotic saline for the final wash, in place of normal saline, consistently increased the final BUP concentration of the liposomes. Formulation 3 yielded a liposomal BUP concentration of 3.5% by weight, higher than any previously reported liposomal BUP formulation. The explanation for this finding is not certain, but may be related to a shrinking of liposomes, allowing a greater number of liposomes into the pellet. The net effect would be an increase in the final BUP concentration.

It was further observed that the drug in these DRV liposomes appeared to be present in two pools, one membrane-associated and the other in the intraliposomal aqueous phase. The distribution varied with the relative concentration of the lipid and drug used, and ratios in the range of 10:1 to 40:60 (membrane to intraliposomal aqueous phase) were observed. Because the two pools release the drug by different mechanisms, each at a different rate, this distribution could be manipulated to control the rate of release of the drug.

II. Analgesic Efficacy

The formulation which yielded the greatest BUP/PL ratio (formulation 3) was evaluated in vivo to determine analgesic efficacy. All experiments were approved by the Institutional Animal Care and Use Committee. Male Swiss-Webster mice weighing 26+3 g (mean+SD) were used. Animals had free access to food and water, and were maintained on 12-hour dark-light cycle. Prior to testing, the hair overlying the abdomen was shaved. Analgesia was assessed using response to cutaneous electrical stimulation. A current generator (model S48, Grass Instruments, Quincy, Mass.) coupled to a constant current unit (model PSIU6F, Grass Instruments, Quincy, Mass.) was used. The current was delivered to the skin surface by touching it gently with two electrodes fashioned from #25 g needles. The vocalization threshold (the current required to produce a vocalization response) was assessed prior to injection of study solutions. This was done by administering two successive stimuli (1 Hz), beginning at 1-mA and increasing in 1-mA increments to a cut-off of 15 mA. Mice who failed to vocalize at 15 mA were excluded from the study.

To determine analgesic duration, mice were injected with liposomal BUP compositions having 0.5 wt % and 3.5 wt % bupivacaine, respectively, formed by dilution (as necessary of formulation 3, above. Free BUP (0.5%), hyperosmotic saline (580 mM), or drug-free liposomes were used as controls. For all groups, 150 ml of test solution was injected subcutaneously using a #25 g needle in 8 mice. After injection, sensory block was assessed at 5, 15, 30 minutes and then at 1, 1.5, 2, 3, 4.5, 6, 9, 12, 14, 16, 17, and 19 hours. Failure to vocalize in response to stimulation with threshold current was taken as analgesia. Testing was continued until two successive tests resulted in vocalization (i.e., absence of analgesia). Duration of sensory block was determined using Kruskall Wallis, with $p<0.05$ considered significant. Results are presented in FIG. 1.

As shown in the Figure, in mice receiving 0.5% free BUP, analgesia was exhibited at 30 minutes, but none was detected at 2 hours. In mice given 0.5% liposomal BUP, all animals demonstrated analgesia at 3 hours, and it was not until 6 hours that analgesia was not detected. For the 3.5% liposomal BUP formulation, all animals had sensory block for 14 hours, and it did not regress in all animals until 19 hours. Thus, a 6 fold increase in analgesic duration was observed when a 0.5% concentration of BUP was injected in liposomes, and this increased to a 28 fold increase when 3.5% liposomal BUP was injected.

Significantly, no obvious signs of toxicity were apparent at this dose, whereas systemic toxic effects of free BUP precluded the administration of doses greater than 0.5%, as they produced toxicity in preliminary studies.

III. Tissue BUP Concentration Post-Administration

Figure 2:
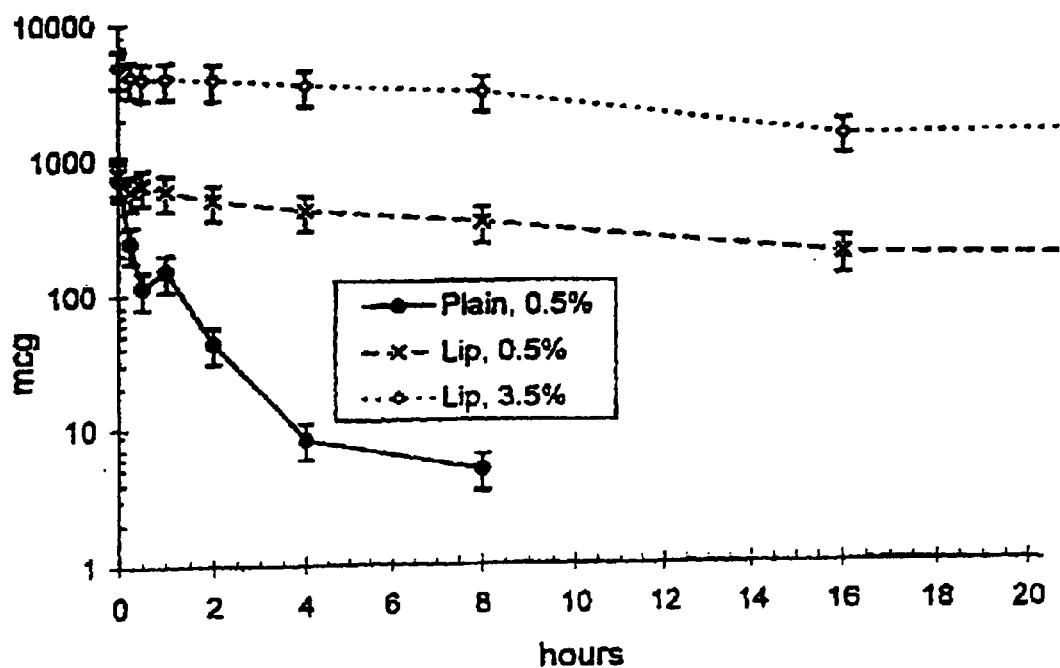
FIG. 2 shows the amount of bupivacaine remaining at the site of injection at a series of time intervals after administration of the compositions of FIG. 1.
Figure 3:
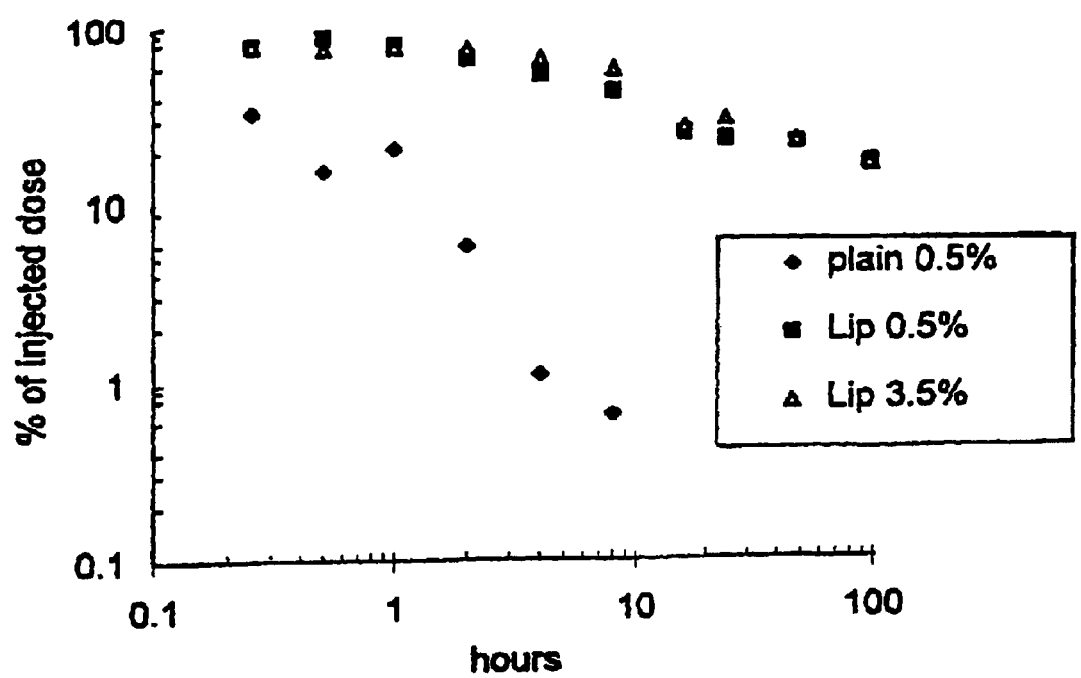
FIG. 3 is a kinetic release profile of the free and liposomal bupivacaine formulations, showing the data of FIG. 2 expressed as a percentage of initial dose.

In a separate group of mice, the amount of drug remaining at the site of injection after administration of 0.5% and 3.5% liposomal BUP (formulation 3) or 0.5% free BUP was determined. Three animals were sacrificed at 0, 0.25, 0.5, 1, 2, 4, and 8 hours after injections of all drug formulations and also at 16, 24, 48 and 96 hours after injection of the liposomal formulations. After sacrifice, a 1-cm2 circular tissue section including the entire area of injection, and extending to the peritoneum, was excised. The tissue was homogenized in 1 ml of isopropanol for 1 min, and then centrifuged at 16,000×G (Eppendorf Centrifuge 5417C, Engelsdorf, Germany). The supernatant was diluted 1:100 in isopropanol, and BUP concentration was determined using HPLC. In vivo release kinetics were done in triplicate. Results are presented in FIG. 2, where the absolute amounts remaining are expressed as mean±SD. FIG. 3 shows the data expressed as percent of initial dose.

As shown in the Figures, free BUP was rapidly redistributed from the injection site, as compared to the liposomal BUP formulations. Four hours after injection, only 1% of the injected dose of free BUP remained at the site (8/750 mg), whereas approximately 54% and 66% of the 0.5% and 3.5% liposomal formulations remained (406/750 mg and 3483/5250 mg, respectively). The redistribution profiles of the 0.5% and 3.5% liposomal BUP formulations were similar. The $t_{1/2}$ was 6.5 hours for the 0.5% liposomal BUP formulation and 6.8 hours for 3.5% liposomal BUP. These similar release profiles, shown in FIG. 3 as percent of injected dose, extended to 96 hours, where 16.8% (126 mg) and 16.5% (868 mg) of the 0.5% and 3.5% liposomal BUP formulations were recovered, respectively.

The slow release of drug from the liposomes provides the benefits of 1) a prolonged residence of drug at the site of injection and 2) a decrease in systemic drug availability. A comparison of FIGS. 2 and 3 shows that much of the injected drug remained associated with the liposomal vehicles after analgesia was no longer exhibited. It is possible that the continued release of BUP produced a weak analgesic effect, which was not detected by our testing technique. Future DRV studies could be directed at decreasing the size of this drug reservoir and achieving more consistent release, perhaps by the use of smaller liposomes. The DRV liposomes in the current study were large, with a mean diameter approximately 2 mm. Although larger liposomes tend to remain longer at the site of injection; a smaller liposome size could result in more thorough release of BUP and less retention in tile depot after the analgesic effect has subsided.

The liposomal BUP formulations described herein significantly prolonged the duration of sensory block after subcutaneous administration, in comparison to free bupivacaine. The present liposomal formulations are distinguished in that they are formed by the DRV technique, thus giving long storage stability, preferably employ DSPC or another high Tm lipid, and have a high (i.e. greater than about 0.15, preferably greater than about 0.25, and more preferably greater than about 0.35) drug-to-lipid ratio. Preparation of the formulations employs a hyperosmotic saline wash, as described above, which results in a high concentration of drug in the final emulsion.

Other local anesthetics may also be used in these formulations. A "local anesthetic", as used herein, refers to a member of the "caine" family of local anesthetic compounds, having physicochemical properties similar to bupivacaine. Structural features common to these compounds include a benzene ring linked via an ester or amide linkage, or, less frequently, a carbamate linkage, to an aliphatic or alicyclic group containing a tertiary or quaternary amine. The length of the linkage, i.e. the distance between the benzene ring and the amine, is typically about 6–9 Å. These compounds include, for example, lidocaine, ropivacaine, levobupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine.

The compositions may be administered subcutaneously, intraperitoneally, topically, and into the neuraxis. Methods for preparing suitable dosage forms are known or will be apparent to those skilled in the art; for example, see *Remington's Pharmaceutical Sciences* (19th Ed., Williams & Wilkins, 1995). The composition to be administered will contain a quantity of bupivacaine in a pharmaceutically effective amount for effecting anesthesia in the subject. Such formulations may allow a single injection to provide prolonged analgesia, and thus obviate the need for repeated injections, catheterization, or use of an infusion pump, as are commonly required with conventional anesthetics. Administration could be performed during or at the end of surgery, and by providing effective pain release could obviate the need for parental narcotics.

While the invention has been described with reference to specific methods and embodiments, it will be appreciated that various modifications may be made without departing from the invention.

References

Bartlett, G R, "Phosphor-us assay in column chromatography." J. Biol. Chem. 234, 466 (1959).

Boogaerts J, Declercq A, Lafont N, Benameur H, Akodad E M, Dupont J C, and Legros F J, "Toxicity of bupivacaine encapsulated into liposomes and injected intravenously: comparison with free solutions." Anesth. Analg. 76(3):553–555 (1993).

Grant G J, Lax J, Susser L, Zakowski M, Weissman T E, and Turndorf H, "Wound infiltration with liposomal bupivacaine prolongs analgesia in rats." Acta Anaesthesiol. Scand. 41(2):204–207 (1997).

Kirby, C. and Gregoriadis, G., "Dehydration-rehydration vesicles: A simple method for high yield drug entrapment in liposomes." Biotechnology 979–985 (1984).

Lafont N D, Legros F J, and Boogaerts J G, "Use of liposome-associated bupivacaine in a cancer pain syndrome." Anaesthesia 51(6):578–579 (1996).

Legros, F. et al., U.S. Pat. No. 5,244,678 (1993).

Mowat J J, Mok M J, MacLeod B A, and Madden T D, "Liposomal bupivacaine. Extended duration nerve blockade using large unilamellar vesicles that exhibit a proton gradient." Anesthesiology 85(3):635–643 (1996).

Stewart, J. C. M., Anal. Biochem. 104, 10 (1959).

Zuidam, N. J. and Crommelin, D. J., "Chemical hydrolysis of phospholipids." J. Pharm. Sci. 84, 1113-9 (1995).

What is claimed is:

1. A method of providing long term local anesthesia comprising:
    a. Administering to a subject in need of such treatment a liposomal local anesthetic formulation for slow release of said local anesthetic formulation,
    b. Wherein said formulation is prepared by a dehydration-rehydration method, in which lyophilized liposomes encapsulating the local anesthetic are rehydrated by agitating in an aqueous medium followed by washing the rehydrated liposomes in an about 300–600 mM hyperosmotic saline solution.

2. The method according to claim 1, wherein the local anesthetic is a member of the "caine" family.

3. The method according to claim 2 wherein the member of the "caine" family is selected form the group consisting of bupivacaine, lidocaine, ropivacaine, levebupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine.

4. The method according to claim 3 wherein the member of the "caine" family is bupivacaine.

5. A method for preparing al liposomal drug having a high drug/lipid ratio, comprising the steps of:
   a. encapsulating the drug in liposomes;
   b. lyophilizing the liposomes;
   c. rehydrating the lyophilized liposomes by agitating in an aqueous medium; and
   d. washing the rehydrated liposomes in an about 300–600 mM hyperosmotic saline solution.

6. The method according to claim 5 wherein the drug is a local anesthetic of the "caine" family.

7. The method according to claim 6 wherein the member of the "caine" family is selected form the group consisting of bupivacaine, lidocaine, ropivacaine, levebupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine.

8. The method according to claim 7 wherein the member of the "caine" family is bupivacaine.

9. A liposomal local anesthetic composition having a high drug/lipid ratio, prepared by encapsulating the local anesthetic in liposomes, lyophilizing the liposomes, rehydrating the lyophilized liposomes by agitating in aqueous medium, and washing the rehydrated liposomes in hyperosmotic saline solution of about 300 mM to 600 mM.

10. The composition according to claim 9 wherein the drug/lipid ratio is at least 0.33 mole/mole.

11. The composition according to claim 9 wherein the local anesthetic is a member of the "caine" family selected from the group consisting of bupivacaine, lidocaine, ropivacaine, levebupivacaine, procaine, chloroprocaine, benzocaine, etidocaine, mepivacaine, prilocaine, ciprocaine, tetracaine, dibucaine, heptacaine, mesocaine, propanocaine, carbisocaine, and butacaine.

12. The composition according to claim 11 wherein the member of the "caine" family is bupivacaine.

* * * * *

UNITED STATES PATENT AND TRADEMARK OFFICE
CERTIFICATE OF CORRECTION

PATENT NO. : 6,926,905 B2  
APPLICATION NO. : 10/620006  
DATED : August 9, 2005  
INVENTOR(S) : Grant et al.

It is certified that error appears in the above-identified patent and that said Letters Patent is hereby corrected as shown below:

On the title page, item 54, in the title delete "LIPOSOMAK" and insert --LIPOSOMAL BUPIVACAINE--.

On the title page, item 63, delete "PCT/US99/06959" and insert --PCT/US99/06958--.

Column 1, line 1, delete "LIPOSOMAK" and insert --LIPOSOMAL BUPIVACAINE--.

Column 7, line 15, should read --A method for preparing a liposomal drug having a high--.

Column 8, line 12, should read --and washing the rehydrated liposomes in a hyperosmotic--.

Signed and Sealed this

Tenth Day of February, 2009

JOHN DOLL  
*Acting Director of the United States Patent and Trademark Office*